(12) United States Patent
Roelvink et al.

(10) Patent No.: US 6,756,044 B1
(45) Date of Patent: Jun. 29, 2004

(54) ANTIGENIC COMPLEXES AND METHODS

(75) Inventors: Petrus W. Roelvink, Olney, MD (US); Joseph T. Bruder, Ijamsville, MD (US); Imre Kovesdi, Rockville, MD (US); Thomas J. Wickham, Germantown, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/617,569

(22) Filed: Jul. 17, 2000

Related U.S. Application Data

(60) Provisional application No. 60/181,289, filed on Feb. 9, 2000.

(51) Int. Cl.[7] .................. A61K 45/00; A61K 39/395; A61K 39/00; A61K 39/23; A61K 47/00; C12N 7/01; C07K 16/100

(52) U.S. Cl. .................. 424/281.1; 424/144.1; 424/184.1; 424/233.1; 424/278.1; 435/235.1; 530/388.2

(58) Field of Search .................. 424/144.1, 153.1, 424/184.1, 205.1, 233.1, 278.1, 281.1; 530/388.2

(56) References Cited

U.S. PATENT DOCUMENTS 5,714,374 A  2/1998  Arnold et al.

FOREIGN PATENT DOCUMENTS

| WO | WO 98/15638 A | 4/1998 |
| WO | WO 99/61051 A | 12/1999 |
| WO | WO 00/18433 A | 4/2000 |

OTHER PUBLICATIONS

Giachelli et al., *Am. J. Pathol.*, 152(2), 353–358 (Feb. 1998).
Toes et al., *Sem. Immunol.*, 10, 443–448 (Dec. 1998).

*Primary Examiner*—James Housel
*Assistant Examiner*—Shanon Foley
(74) *Attorney, Agent, or Firm*—Leydig, Voit & Mayer, Ltd.

(57) ABSTRACT

The present invention provides a complex that includes a virion having a ligand that recognizes an epitope present on an immune effector cell surface and at least a first nucleic acid encoding a first non-native antigen. The invention also provides a library including a plurality of such complexes, in which antigens of at least two of the plurality are different. Using such reagents, the invention provides a method of precipitating an immune response within an immune effector cell, wherein such a complex is delivered to the cell under conditions sufficient for the cell to mount an immune response to the antigen. When applied in vivo, the method can serve to immunize an animal from the pathogen. Moreover, using a library including a plurality of complexes, which contains at least one test antigen, the invention provides a method of assessing the antigenicity of the test antigen.

43 Claims, No Drawings

ANTIGENIC COMPLEXES AND METHODS

CROSS REFERENCE TO RELATED APPLICATION

The present patent application claims priority to U.S. Provisional Patent Application No. 60/181,289, filed Feb. 9, 2000.

TECHNICAL FIELD OF THE INVENTION

The present invention pertains to antigenic complexes and methods of inoculating and immunizing animals.

BACKGROUND OF THE INVENTION

The identification of pathogenic organisms and viruses has led to the development of successful protocols for immunizing healthy individuals against such organisms. Early protocols involved exposing healthy individuals to live or attenuated pathogens to induce immune responses against the pathogens. With respect to many pathogens, such live or attenuated vaccines remain superior to other vaccines because of their tendency to elicit a broad level protective response. Other disorders, however, are caused or spread by pathogens less amenable to this approach. For example, it has proven difficult to develop or store live or attenuated vaccines derived from several common pathogens. Still other pathogens simply are not sufficiently antigenic to generate a sufficient (or even any) response in a host animal to be useful as a vaccine, whether through evolved stealthing defenses (e.g., HIV, herpes, etc.), limited presentation of antigen, genetic drift (e.g., influenza), or other proclivities. Of course, the possibility of actually causing the disease against which protection is intended (e.g., polio, measles, etc.) remains a major concern associated with this approach.

An alternative to the use of live/attenuated pathogen vaccines is to use antibodies raised against antigens associated only with an identified pathogen. Such approaches can be effective in some instances. However, no assurance can be had that any antibodies raised against a putative antigen will effectively protect against the pathogen providing the antigen. Thus, it is frequently necessary to test a large number of putative antigens isolated from a pathogen, rendering such approaches relatively costly and time consuming. Also, such approaches generally do not elicit the broad level of protective response associated with live vaccines.

Genetic or peptide immunization has emerged as an alternative to conventional vaccines. This technology involves inoculating DNA encoding a pathogen protein, or an isolated pathogen protein, into the host. Risk of infection is greatly reduced, and the DNA or protein vaccines can be delivered to cells not normally infected by the pathogen. Compared to conventional vaccines, the production of DNA or peptide vaccines is straightforward, and DNA and protein are considerably more stable than live/attenuated vaccines. However, some DNA or protein vaccines are not effective against certain pathogens. Indeed, vaccine approaches that deliver entire proteins may direct the immune response against immunodominant epitopes only, and not against subdominant epitopes (e.g., EBV latent membrane protein). Alternatively, such approaches can direct an immune response against epitopes subject to antigenic variation, and in some instances, such approaches can actually result in tolerance to the pathogen (e.g., a tumor or a microbe), rather than immunity (see, e.g., Toes et al., *Proc. Nat. Acad. Sci. (USA)* 94, 14660–65 (1997); Toes et al., *Proc. Nat. Acad. Sci. (USA)*, 93, 7855–60 (1996); Toes et al., *J. Immunol.*, 156, 3911–18 (1996); Aichele et al., *Proc. Nat. Acad. Sci. (USA)*, 91, 444–48 (1994); Aichele et al., *J. Exp. Med.*, 182, 261–66 (1995)).

Other recent advances in vaccine technology have focused on the manner in which cellular immunity is acquired in the first instance. Recognition and destruction of at least some pathogens is performed principally by $CD8^+$ cytotoxic T lymphocytes (CTLs). The mounting of a CTL immune response requires that "foreign" proteins undergo intracellular processing to peptide fragments, a function performed with high efficiency by professional antigen presenting cells (APCs), such as B-cells, dendritic cells, lymphoid fibroblasts, Langerhans cells, macrophages, monocytes, peripheral blood fibrocytes, etc., and potentially other cells such as cortical thymus epithelial cells, Ia-Thy 1-cells, peritoneal exudate cells, and the like. The processed peptide fragments ultimately are presented at the cell surface complexed with major histocompatability complex (MHC) class I molecules, which constitute the first stimulatory signals recognized by a CTL.

Processing of antigens presented by class I MHC generally involves endogenous synthesis and cytoplasmic processing not involving endosomes. While, under some circumstances, exogenous antigens can enter the cytoplasm for processing by the nonendosomal pathway and presentation by class I MHC, typically, exogenous antigens are internalized and processed through endosomes for presentation by class II MHC. To exploit this biology, APCs pulsed with proteins or DNA have been employed in vaccines. Typically, dendritic cells are harvested and pulsed with the protein or DNA and then cultured to activate MHC-I or MHC-II responses. These cells can be used subsequently in vivo or in vitro to present the antigens to CTLs. While these approaches may prove promising, a matter of concern when using APCs as carriers is that isolating even limited amounts of such cells is labor-intensive. Moreover, MHC class II-deficient APCs, expressing only MHC-I often fail to induce protection (Schnell et al., *J. Immunol.*, 164(3), 1243–50 (2000)). This demonstrates the desirability of achieving both types of response.

In addition to the limitations of current vaccine technologies, the identification of suitably antigenic proteins, peptides, or other moieties from many species of pathogen remains elusive. Considering these, and other, drawbacks, a need remains for improved strategies for identifying suitable antigens and for using them to inoculate animals.

BRIEF SUMMARY OF THE INVENTION

The present invention provides a complex that includes a virion having a ligand that recognizes an epitope present on an immune effector cell surface and at least a first nucleic acid encoding a first non-native antigen. The invention also provides a library including a plurality of such complexes, in which antigens of at least two of the plurality are different.

Such reagents are useful both in research and in the clinic. Thus, for example, the invention provides a method of precipitating an immune response within an immune effector cell, wherein such a complex is delivered to the cell under conditions sufficient for the cell to mount an immune response to the antigen. When applied in vivo, the method can serve to immunize an animal from the pathogen. Moreover, using a library including a plurality of complexes, which contains at least one test antigen, the invention provides a method of assessing the antigenicity of the test antigen. These and other aspects of the present invention, as well as additional inventive features, will be apparent upon reading the following detailed description.

DETAILED DESCRIPTION OF THE INVENTION

Within the inventive complex, the ligand on the virion typically (but need not be) proteinaceous. Examples of suitable ligands include (but are not limited to) short (e.g., about 6 amino acids or less) linear stretches of amino acids recognized by integrins, as well as polyamino acid sequences such as polylysine, polyarginine, etc. Inserting multiple lysines and/or arginines provides for recognition of heparin and DNA, and an RGD sequence can be used as a ligand to bind integrins, such as are present on immune effector cells. Tandem repeats of lysine, arginine, and/or histidine residues (e.g., three or more, five or more, or even as many as ten or more tandem lysine residues, tandem arginine residues, tandem histidine residues, or tandem mixtures of lysine or histidine) can be similarly employed. Other ligands can be specific for particular substrates, such as, for example, immunoglobulin-like molecules (e.g., FABs, ScABs, etc.), or known specific ligands (e.g., CD40L that recognizes the CD40 antigen). Thus, it will be apparent that, in some embodiments, the ligand is native to the virion (i.e., being present in a wild-type virus from which the virion is derived), but in other embodiments the ligand is a non-native ligand.

The ligand can be any moiety that binds with relative specificity to a substrate present on the surface of an immune effector cell (e.g., a T-lymphocyte or a B-lymphocyte, a natural killer cell, a granulocyte, a macrophage, a monocyte, a polymorphonucleocyte, a dendritic cell, etc.). Such a cell surface binding site can be any suitable type of molecule, but typically is a protein (including a modified protein such as a glycoprotein, a mucoprotein, etc.), a carbohydrate, a proteoglycan, a lipid, a mucin molecule, or other similar molecule. Examples of potential cell surface binding sites include, but are not limited to, heparin and chondroitin sulfate moieties found on glycosaminoglycans; sialic acid moieties found on mucins, glycoproteins, and gangliosides; and common carbohydrate molecules found in membrane glycoproteins, including mannose, N-acetyl-galactosamine, N-acetyl-glucosamine, fucose, and galactose. As immune effector cells typically are classified by the presence of various cell-surface proteins, many suitable proteins are known in the art.

The inventive complex is useful for eliciting an immune response within a derived (i.e., target) immune effector cell, typically an APC. In many applications, dendritic cells are preferred target APCs because using the CD40 ligand (CD40 L) as a targeting ligand also facilitates the priming of CD8$^+$ cells (see, e.g., Toes et al., *Sem. Immunol.*, 10, 443–48 (1998)), further enhancing the efficacy of the invention. Where dendritic cells are the desired target, the ligand can recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc. Preferably, where dendritic cells are targeted, the ligand recognizes the CD40 cell surface protein, such as, for example, a CD-40 (bi)specific antibody fragment or a domain derived from the CD40L polypeptide.

Where macrophages are the desired target, the ligand can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor β, HLA Class I, Sialoadhesin, siglec-5, and the toll-like receptor-2 (TLR2).

Where B-cells are the desired target, the ligand can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD 19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fcα, Fcγ, Fcε, etc.), IgM, gp200-MR6, Growth Hormone Receptor (GH-R), ICAM-1, ILT2, CD85, MHC class I and II molecules, transforming growth factor receptor (TGF-R), α4β7 integrin, αiibβ3 integrin, αLβ2 integrin, and αvβ3 integrin.

Where fibrocytes are the desired targets, the ligand can recognize a protein found on fibrocyte cell surfaces such as major histocompatability complex molecules, co-stimulatory molecules, and adhesion molecules, such as, for example, CD11a, CD13, CD34, CD45, CD54, CD58, CD80, CD86, HLA-DQ, HLA-DR, HLA-DP, and MHC-I and -II molecules. Of course, other cell types can be similarly targeted using domains known to be present within the surfaces of the desired cell.

In addition to the virion having the ligand, the complex also includes a (i.e., at least one) nucleic acid encoding a first non-native antigen. The antigen is "non-native" in that it is not present on a wild-type virus corresponding to the source from which the virion is derived. With this stricture in mind, the antigen can be any moiety to which it is desired to effect an immune response. Typically, the antigen is an antigenic peptide derived from a pathogen (e.g., a virus, a bacterium, a spore or fungus, a parasite, etc.) or from a cancerous cell. Examples of some suitable antigens include, but are not limited to, viral antigens (e.g., from HIV GP120, Env, gag, pol or nef proteins or polypeptides, EBV latent membrane protein, etc.), endoglin, and tumor-associated antigens (TAAs) (e.g., BAGE, carcinoembryonic antigen (CEA), CASP-8, β-catenin, CDK-1, ESO-1, gp75, gp100, MAGE-1, -2, and -3, MART-1, mucins (MUC), MUM-1, p53, PAP, PSA, PSMA, ras, tyrosinase, trp-1 and -2, etc.). In another embodiment, an antigen can be a synthetic polypeptide (e.g., an HLA-A2-restricted gp100 peptide (see, e.g., Rosenberg et al., Nat. Med., 4, 321–27 (1998)). For example, such an antigenic polypeptide can include a series of antigenic epitopes, such as between about 1 and about 15 (e.g., between about 5 and 10) such antigenic epitopes. Indeed, the antigenic properties of the inventive vaccine can be enhanced against that pathogen by using such synthetic antigens having epitope domains derived from the same pathogen. To facilitate processing and proper presentation, preferably each of such domains contains between about 5 and about 10 amino acids (e.g., about 8 amino acids) and/or is separated from other domains by polyamino acid spacers (e.g., polyalanine). Similarly, antigenicity also can be enhanced where the complex includes a plurality of such nucleic acids (i.e., encoding more than one first antigen).

Expression of the nucleic acid encoding the first antigen within the immune effector cells can permit the stimulation of an MHC-I response against the antigen. Moreover, in some embodiments, it is desirable for the complex to have a plurality of nucleic acids encoding antigens (e.g., to stimulate immune responses against multiple sites on a pathogen or to stimulate immune responses against multiple pathogens). Thus, the nucleic acid preferably is expressed within immune effector cells, and more preferably APCs. To facilitate expression, the nucleic acid encoding the first antigen is operably linked to a promoter that is active within the desired immune effector cell.

Preferably, in addition to the ligand and the nucleic acid encoding the first antigen, the complex also includes at least one second non-native antigen. This antigen can, as is the case for the ligand, be displayed on the surface of the virion, but it need not be so displayed (e.g., it can be a latent antigen), so long as it elicits an immune response. The second antigen can be any suitable antigenic moiety, such as those set forth above. The presence of the second antigen can facilitate an MHC-II response against the antigen. In many embodiments, to enhance the potency of the immune response, the first (i.e., encoded) antigen(s) and the second (i.e., surface) antigen(s) are derived from the same pathogen. Such a strategy facilitates the generation of both an MHC-I and MHC-II response to the pathogen. In this respect, a particularly preferred embodiment is for at least one first antigen to be the same as at least one second antigen.

To facilitate attachment of the ligand to the desired cell, the ligand should be displayed on the surface of the virion within the complex. Suitable display can be accomplished by any desired means. For example, the ligand can be a domain present within a bi- or multi-specific protein (e.g., a bi-specific antibody), another domain of which selectively binds to a moiety present on the virion. In another embodiment, the ligand can be integrally connected to the virion. For example, the virion can include at least one chimeric protein having at least one first domain derived from a viral capsid protein and at least one-second domain comprising the ligand. Within such chimeric proteins, the viral capsid protein domains, as well as the ligand domains, can be full length or truncated. Of course, the virion can include a plurality of such proteins. In yet another embodiment, the ligand can be chemically conjugated to the virion by methods known in the art.

The virion is composed of viral capsid proteins, and it can be, but it need not be, an intact virus. Indeed, the virion can be a virus-like particle (VLP), empty capsid, or other viral-derived structure that has a lumen and a surface. However, preferably the virion is an intact virus, in which instance the nucleic acid encoding the first nucleic acid comprises a viral genome, typically also including encoding one or more of the viral capsid proteins making up the virion. Where the nucleic acid is a viral genome, it need not be complete, and, indeed, for many applications, the genome preferably contains one or more mutations interfering with viral replication. In some embodiments, the vector most preferably is replication incompetent except in packaging cells. Any suitable manipulation of the viral genome can be applied to achieve this end, many of which are known in the art. Thus, for example, where the virion and nucleic acid constitute an adenovirus, it can have replication-inactivating mutations, e.g., within the E1a, E1b, E2, and/or E4 regions of the genome. Similarly, where the virus is HSV, it can have inactivating mutations in one or more immediate early genes (e.g., ICP4, ICP27, ICP0) to render it replication incompetent. In other embodiments, for example where mimicry of a live virus is desired, it is desirable for the virus to be replication competent.

Structurally, the virion can be enveloped or non-enveloped, and it can be derived from any desirable type of virus. Preferably, the virion is derived from a virus useful as a gene-transfer vector, such as, for example, herpesviruses (e.g., Herpes Simplex, Epstein-Barr, pox, etc.), adenoviruses, adeno-associated viruses (AAV), and other viruses known in the art. As considerable advances have been made in engineering functional chimeric adenoviral coat proteins, in embodiments in which ligands and/or second antigens are desired to be integral with the virion, preferably the virion is derived from an adenoviral capsid. In this respect, any chimeric protein desirably has at least one domain representing the ligand (or second antigen) and at least one other domain derived from an adenoviral coat protein (e.g., fiber, hexon, penton, pIIIa, pVI, pIX).

To further direct the virion to the desired immune effector cells, preferably its natural tropism for other types of cells is attenuated or eliminated. Methods suitable for attenuating native viral tropism are known in the art. For example, adenoviral-based virions can have one or more mutant adenoviral fiber protein(s) exhibiting reduced affinity for a native adenoviral cellular receptor (see, e.g., International Patent Application WO 98/54346 (Wickham et al.)). Moreover, an adenovirus-derived virion can include one or more recombinant penton base protein(s) lacking a native RGD sequence to reduce cell binding via $\alpha_v$ integrins (see, e.g., U.S. Pat. No. 5,559,099 (Wickham et al.) and U.S. Pat. No. 5,731,190 (Wickham et al.)). Similarly, an adenovirus-derived virion can include one or more recombinant hexon(s) lacking a native sequence (e.g., HVR) to reduce its ability to be recognized by a neutralizing antibody (see, e.g., International Patent Application WO 98/40509 (Crystal et al.)). In other embodiments, a herpesvirus-derived virion can have mutant envelope glycoproteins lacking cell-surface ligands (see, e.g., International Patent Application WO 99/06583 (Glorioso et al.)).

Preferably, the immune response elicited against the complex is specific to either the first (i.e., surface) and/or second (i.e., encoded) antigen(s). Thus, the virion preferably elicits less virion-specific immunogenicity in a host animal than does a corresponding wild-type virion. To facilitate this, the virion can be engineered to lack a native immunodominant epitopes, such as are present in adenovirus, for example, on the viral hexon protein (see, e.g., International Patent Application WO 98/04509). Similarly, the virus can be engineered to lack one or more glycosylation or phosphorylation site(s). Alternatively, the virion can be conjugated to a lipid derivative of polyethylene glycol comprising a primary amine group, an epoxy group, or a diacylglycerol group. Without being bound by any particular theory, such modifications are believed to mask the virion, at least in part, from scavenging, particularly by the cells of the reticulo-endothelial system.

Regardless of whether the virion is an intact virus or a VLP, the complex is useful for delivering the nucleic acid to an immune effector cell such that the nucleic acid is expressed within the immune effector cell to produce the first antigen. To facilitate this, the complex can include adjunct constituents for facilitating transduction of the cells (e.g., one or more liposomes), and the presence of such adjuncts is preferred when the virion is other than an intact virus. To further promote immune activation, the complex can include at least one second nucleic acid sequence encoding a factor that activates an immune effector cell. For example, the factor can be a cytokine, such as granulocyte colony stimulating factor (CSF), monocyte CSF, granulocyte and monocyte CSF, interleukins 1–12, tumor necrosis factor-$\alpha$ or -$\beta$, macrophage inflammatory protein (MIP)-1-$\alpha$ or -$\beta$, MIP-2, interferon-$\gamma$ (IFN-$\gamma$), etc. In embodiments where dendritic cells, macrophages, or other APCs are the targeted immune-effector cells, the factor can be CD40-L or osteopontin (or active fragments of these proteins), as these accentuate IL-12 and attenuate IL-10, which is associated with activation of the CD40 protein and the specificity of the response through initiation of the TH-1 and TH-2 subsets. Similarly, the second nucleic acid can encode a superantigen (e.g., a protein, such as are found on some bacteria, that prime cells of the immune system). In other embodiments, the second nucleic acid can encode an anticancer agent, e.g., a cytokine, an enzyme that converts a prodrug to a toxin (e.g., HSV tk), an apoptotic or an anti-angiogenic agent, many of which are known in the art.

The second nucleic acid can be present within a larger nucleic acid molecule that also includes the first nucleic acid (which is typically the case, where the capsid or virion includes an intact virus), or the two nucleic acid molecules can be within different nucleic acids, if desired. Of course, the second nucleic acid should be operably linked to a promoter sufficient to drive expression of the encoded factor within the desired immune effector cells, as described above. As with the first nucleic acid, any suitable promoter can be employed with respect to the second nucleic acid, such as a constitutive promoter (e.g., a viral inmmediate early promoter), a tissue-specific promoter, a regulatable promoter (e.g., metallothionin promoter, tetracycline-responsive promoter, RU486-responsive promoter, etc.), or other desired promoter. Indeed, the first and second nucleic acids can share the same promoter, such as, for example, separated by internal ribosome entry sites (IRES). In another embodiment, the first and second nucleic acids are on opposite sides of a strong bi-directional promoter, many of which are known in the art (see, e.g., Lee et al., *Mol Cells.*, 10(1), 47–53 (2000), Dong et al., *J. Cell. Biochem.*, 77(1), 50–64 (2000), and Li et al., *J. Cell. Biochem.*, 273(43):28170–7 (1998)).

The complex can be made by standard methods. Typically, the virions are constructed by producing viral capsid or coat proteins within packaging cells appropriate for the type of virus (e.g., HEK 293 cells, Vero cells, etc.) within which they will associate to form the virions. Ligands and antigens can be attached to, or incorporated into, the virions by known methods (see, e.g., U.S. Pat. Nos. 5,965,541, 5,962,311, 5,846,782, 5,770,442, 5,731,190, 5,712,136, and 5,559,099). Of course, where the nucleic acid(s) are included within a viral genome, the genome will be packaged within the virion during synthesis. Conversely, where at least one nucleic acid is extragenomic, it is included within the complex by admixing it with the virion under suitable conditions, along with other components of the complex, such as liposomes (see, e.g., U.S. Pat. No. 5,928,944).

The virions within the complex can be homogeneous, in which the antigens, ligands, capsids and nucleic acids of each member are identical or substantially identical. In other applications, the complex can be heterogeneous (i.e., a "library"). Indeed, the invention provides a library including a plurality of complexes, each comprising a virion as described above and at least a first nucleic acid encoding a first non-native antigen. The library is heterogeneous in that antigens of at least two of the plurality of the complexes are different. Of course, the virions within the library also can include ligands and other nucleic acids as described above (e.g., encoding antigens, cytokines, or other factors of interest). Typically, the library is constructed by generating a random or semirandom population of putative antigens that are variously associated with the virion as described above. For example, the putative antigens can be generated by proteolysis of proteins derived from a desired pathogen, the products of which can be fused to the capsid or to bi-specific molecules (as appropriate). Alternatively, mRNA or genomic DNA libraries from the desired pathogen can be randomly amplified, or digested, to result in fragments that can be subcloned into vectors suitable for inclusion within the complex. For association with the virion, for example, the fragments can be cloned in-frame with viral capsid proteins (including truncated derivatives thereof) to generate chimeric capsid proteins containing antigenic domains. Similarly, the fragments can be cloned so as to be operably linked to the promoter suitable for expression within the desired immune effector cells, as described above.

The inventive complex (or library) can be used to infect or transduce cells, typically immune effector cells. For delivery into a host animal, the complex (or library) can be incorporated into a suitable carrier to form a pharmaceutical or pharmacological composition. As such, the complex can be formulated and/or administered with a pharmacologically acceptable carrier (e.g., a pharmaceutically-acceptable carrier). Any suitable carrier is within the scope of the invention. The exact formulation, of course, depends on the nature of the desired application (e.g., cell type, mode of administration, etc.), and many suitable formulations are known in the art (see, e.g., U.S. Pat. No. 5,559,099). Of course, the pharmaceutical composition can include other constituents, such as, for example, other agents that activate or enhance an immune response (e.g., (complete) Freund's reagent).

The complex, library, and pharmaceutical composition of the present invention are useful for eliciting immune responses within a desired immune effector cell, typically an APC. Thus, the invention provides a method of eliciting such a response using a complex comprising a virion and a first nucleic acid encoding a first non-native antigen. The immune response can be or comprise presentation of at least one of the antigens as an MHC-I-constrained moiety (an "MHC-I response") or as an MHC-II-constrained moiety (an "MHC-II response"). Preferably, the method results in both MHC-I and MHC-II responses. To promote both types of responses, preferably the virion has at least one second non-native antigen displayed on its surface, in addition to including the nucleic acid encoding the first antigen.

The method can be employed in vivo, typically within a mammal, or ex vivo or in vitro on isolated immune effector cells. For in vitro application, suitable cells (preferably APCs) can be isolated from the skin, spleen, bone marrow, other lymphoid organs, lymph nodes, or blood using methods known in the art (see, e.g., Unanue, *Fundamental Immunology*, Third Edition, Paul (ed.), Raven Press, Ltd.: New York., pp. 119–21 (1993); U.S. Pat. No. 5,962,318). In other protocols, peripheral blood monocytes can be isolated and cultured to mature them into dendritic cells (see, e.g., Rossi et al., *Immunol. Lett.*, 31(2), 189–97 (1992)). After isolation and purification, the cells can be exposed to the inventive complex (or library) and maintained under conditions sufficient for them to develop an immune response (typically, incubation for about a day or two under appropriate culture conditions). To enhance antigen presentation, preferably the cells also are exposed to one or more activation factors (such as the cytokines discussed above). Such factors can be delivered exogenously, for example in the medium in which the cells are cultured. Alternatively, where the complex includes a nucleic acid encoding such factors, its expression within the cells can effectively deliver the factor to the cells. In any event, following a suitable incubation, the cells can be monitored to assess their immune response by any suitable method (e.g., flow cytometry, FACS, elispot analysis, etc.). Thereafter, the cells can be propagated or maintained as desired. Such cells can be reintroduced into mammals in vivo for presenting the MHC-I and/or MHC-II antigens to immunize the mammal against the antigen(s) presented to the immune effector cells.

Where a library (such as described above) is employed, the method affords the ability to assess the antigenicity of at least one "test," or putative, antigen. The method is conducted similarly as described above, except that the relative strengths of the response to the test antigen(s) are compared within the population of cells. Typically, after exposure to the library, the cells are subjected to subcloning (e.g., by limiting dilution), plated separately, and then expanded before assessing the strength of the response to the library. Colonies exhibiting a strong response to the antigen can be analyzed to determine the identity of the antigen, which then can be employed as a vaccine.

When the method is applied in vivo, the invention provides a method of inoculating or immunizing an animal. In accordance with the method, a complex (or library), such as is set forth above, is introduced into the mammal under conditions sufficient for the mammal to mount an immune response to the antigens. While many methods of inoculation are known in the art, subdermal or subcutaneous injection is favored for many applications. For maximally targeting immune effector cells, especially in vivo, preferably the complex includes at least one ligand displayed on the surface of the virion, as described above, recognizing an epitope present on a desired type of immune effector cell, preferably an APC. The presence of the ligand permits the complex to be targeted preferentially to the immune effector cells. Also, preferably the virion is further engineered (as discussed above) to reduce any tropism that corresponding wild-type viruses might exhibit towards non-immune effector cells, to maximally direct the complex to the desired immune effector cells. To heighten the response of the immune effector cells within the mammal, preferably the complex further includes at least one nucleic acid sequence encoding a factor that activates the cell, such as those cytokines, CD40-L, or osteopontin, as described above. Expression of the nucleic acid, thus, activates the cell to heighten the immune response.

EXAMPLE

While one of skill in the art is fully able to practice the instant invention upon reading the foregoing detailed description, the following example will help elucidate some of its features. In particular, it describes the construction of an adenoviral vector having a non-native ligand recognizing an epitope present on an immune effector cell, a first nucleic acid encoding a non-native antigen, and a second nucleic acid encoding an activator of APCs. Of course, as this example is presented for purely illustrative purposes, it should not be used to construe the scope of the invention in a limited manner, but rather it should be seen as expanding upon the foregoing description of the invention as a whole.

The procedures employed in this example, such as gene cloning, vector manipulation, and cell culture are familiar to those of ordinary skill in this art (see, e.g., Sambrook et al., *Molecular Cloning: A Laboratory Manual*, 2 d edition, Cold Spring Harbor Press (1989)). As such, and in the interest of brevity, experimental protocols are not recited in detail.

To construct the vector, a sequence encoding an RGD motif is engineered into the fiber gene of a replication-deficient adenovirus so as to fuse it to the HI loop of the encoded fiber, as previously described (see U.S. Pat. No. 5,965,541). The RGD motif targets the virus to dendritic cells by binding cell-surface heparin molecules. Additionally, a hemagglutinin (HA) tag is engineered into the chimeric fiber adjacent to the RGD motif, which facilitates purification of the virus. This construct can be engineered within a plasmid encoding the fiber gene, the sequence of which is known.

The nucleic acids are introduced into the E1 region of the adenoviral genome as a recombinant expression cassette cloned into a plasmid encoding the E1 region of the adenoviral genome. This cassette includes a bi-directional promoter that directs transcription of two coding polynucleotides in opposite directions. In one direction, the promoter is operably linked to the gene encoding osteopontin (Ono et al., *Mol. Immunol.*, 32(6), 447–48 (1995)). In the other direction, the promoter is operably linked to a nucleic acid encoding a polyepitope "string of beads" antigen (see, e.g., Toes et al., *Proc. Nat. Acad. Sci. (USA)*, 94(26), 14660–65 (1997)).

Each of the desired constructs within plasmids are then recombined back into the "master-vector" adenoviral backbone using standard *E. coli* transformation and manipulation techniques. The master vector then is transfected into packaging cells by standard protocols and incubated for about 5–7 days. Because of the vector's altered tropism (by virtue of the manipulations to the fiber), it is desirable to employ a cell expressing a ligand that can bind the HA tag in the fibers. One such suitable cell line, derived from HEK-293 cells (i.e., 293-HA cells), is known in the art (see, e.g., International Patent Application WO 98/54346). Following this initial incubation, the supernatant is collected and used to infect fresh packaging cells, which are again incubated for about 5–7 days. After several rounds of amplification, standard assays (e.g., Southern blots, hybridization, cell-binding, etc.) are used to analyze the resultant recombinant adenoviral vector.

A stock of the resultant vector then is exposed to cultured dendritic cells under conditions to facilitate infection of the cells. Following several days, the cells are processed to determine that the vectors have, in fact, infected them. The cells then are assayed, e.g., by Northern hybridization and/or Western blot, to determine that the nucleic acids encoding the osteopontin and the string of beads have been expressed. Another population of the cells is assayed to demonstrate that the string of beads is presented as an MHC-I-constrained epitope and that the HA epitope is expressed in a MHC-II-constrained manner. Yet another population of the cells is assayed for the effect of the osteopontin, e.g., by assaying for activation of the CD40 protein and/or for IL-12/IL-10 levels.

Incorporation by Reference

All sources (e.g., inventor's certificates, patent applications, patents, printed publications, repository accessions or records, utility models, world-wide web pages, and the like) referred to or cited anywhere in this document or in any drawing, Sequence Listing, or Statement filed concurrently herewith are hereby incorporated into and made part of this specification by such reference thereto.

Interpretation Guidelines

The foregoing detailed description sets forth "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used herein, singular indicators (e.g., "a" or "one") include the plural, unless otherwise indicated. The term "consisting essentially of" indicates that unlisted ingredients or steps that do not materially affect the basic and novel properties of the invention can be employed in addition to the specifically recited ingredients or steps. In contrast, the terms "comprising" or "having" indicate that any ingredients or steps can be present in addition to those recited. The term "consisting of" indicates that only the recited ingredients or steps are present, but does not foreclose the possibility that equivalents of the ingredients or steps can substitute for those specifically recited.

What is claimed is:

1. A complex comprising (a) a virion having a surface and a lumen and comprising viral capsid proteins, (b) at least one non-native ligand displayed on the surface, which at least one ligand recognizes an epitope present on an immune effector cell, (c) at least one first nucleic acid encoding at least one first non-native antigen, and (d) at least one non-native second antigen displayed on the surface.

2. The complex of claim 1, wherein at least one ligand recognizes a protein on an antigen presenting cell.

3. The complex of claim 1, wherein at least one ligand recognizes CD-40.

4. The complex of claim 1, wherein at least one ligand comprises an RGD motif or three or more tandem lysine and/or histidine residues.

5. The complex of claim 1, wherein an antigen is a gene product from a pathogen or a malignant cell.

6. The complex of claim 1, wherein an antigen is a synthetic polypeptide having from about 1 to about 15 antigenic domains.

7. The complex of claim 1, wherein at least one first antigen is the same as at least one second antigen.

8. The complex of claim 1, wherein the virion comprises at least one chimeric protein comprising at least one first domain derived from a viral capsid protein and at least one second domain comprising at least one second antigen or at least one ligand.

9. The complex of claim 1, further comprising a liposome.

10. The complex of claim 1, wherein the virion is non-enveloped.

11. The complex of claim 1, wherein the virion elicits less virion-specific immunogenicity in a host animal than does a corresponding wild-type virion.

12. The complex of claim 1, wherein the virion comprises an adenoviral capsid.

13. The complex of claim 1, wherein the first nucleic acid comprises a viral genome.

14. The complex of claim 1, wherein the nucleic acid is expressed in an immune effector cell.

15. A pharmaceutical composition comprising (a) the complex of claim 1, and (b) a physiologically-acceptable carrier.

16. The pharmaceutical composition of claim 15, wherein the complex comprises at least one second nucleic acid sequence encoding a polypeptide that activates an immune effector cell.

17. The pharmaceutical composition of claim 16, wherein at least one polypeptide comprises a domain derived from CD40-L or osteopontin.

18. The pharmaceutical composition of claim 16, wherein the polypeptide is a cytokine.

19. The complex of claim 1, further comprising at least one second nucleic acid sequence encoding at least one polypeptide that activates an immune effector cell.

20. The complex of claim 19, wherein at least one polypeptide comprises a domain derived from CD40-L or osteopontin.

21. The complex of claim 19, wherein at least one polypeptide is a cytokine.

22. The complex of claim 19, wherein at least one polypeptide is CD40-L.

23. The complex of claim 19, wherein at least one polypeptide is osteopontin.

24. A method of inoculating a mammal, the method comprising introducing the complex of claim 1 into a mammal under conditions sufficient for the mammal to mount an immune response to at least one first non-native antigen.

25. The method of claim 24, wherein the mammal comprises an immune effector cell, and wherein at least one immune response comprises an MHC-I response within the immune effector cell.

26. The method of claim 24, wherein the mammal comprises an immune effector cell, and wherein at least one immune response comprises an MHC-II response within the immune effector cell.

27. The method of claim 24, wherein the complex comprises at least one second nucleic acid sequence encoding at least one polypeptide that activates an immune effector cell, which is expressed within the mammal under conditions sufficient to activate the immune effector cell.

28. The method of claim 27, wherein the polypeptide comprises a domain derived from CD40-L or osteopontin.

29. The method of claim 27, wherein the polypeptide is a cytokine.

30. The method of claim 27, wherein at least one polypeptide is CD40-L.

31. The method of claim 27, wherein at least one polypeptide is osteopontin.

32. A method of immuning a mammal, the method comprising introducing a complex comprising (a) a virion having a surface and a lumen and comprising viral capsid proteins, (b) at least one first nucleic acid encoding at least one first non-native antigen, and (c) at least one second non-native antigen displayed on the surface into a mammal under conditions sufficient for the mammal to mount at least one immune response to at least one of the antigens.

33. The method of claim 32, wherein the complex further comprises at least one non-native ligand displayed on the surface, which recognizes an epitope present on an immune effector cell.

34. The method of claim 32, wherein the mammal comprises an immune effector cell, and wherein at least one immune response comprises an MHC-I response within the immune effector cell.

35. The method of claim 32, wherein the mammal comprises an immune effector cell, and wherein at least one immune response comprises an MHC-II response within the immune effector cell.

36. The method of claim 32, wherein the complex comprises at least one second nucleic acid sequence encoding at least one polypeptide that activates an immune effector cell, which is expressed within the mammal under conditions sufficient to activate the immune effector cell.

37. The method of claim 36, wherein at least one polypeptide comprises a domain derived from CD40-L or osteopontin.

38. The method of claim 36, wherein the polypeptide is a cytokine.

39. The method of claim 36, wherein at least one polypeptide is CD40-L.

40. The method of claim 36, wherein at least one polypeptide is osteopontin.

41. A complex comprising (a) a virion having a surface and a lumen and comprising viral capsid proteins, (b) at least one first nucleic acid encoding at least one first non-native antigen, and (c) at least one non-native second antigen displayed on the surface.

42. A method of immunizing a mammal, the method comprising introducing the complex of claim 41 into a mammal such that the mammal mounts an MHC-I immune response against the first non-native antigen and an MHC-II immune response against the second non-native antigen.

43. A pharmaceutical composition comprising (a) the complex of claim 41, and (b) a physiologically-acceptable carrier.

* * * * *